United States Patent [19]

Lassen

[11] Patent Number: 4,804,669

[45] Date of Patent: Feb. 14, 1989

[54] TREATMENT OF PAIN WITH A PIPERIDINE

[75] Inventor: Jørgen B. Lassen, Glostrup, Denmark

[73] Assignee: A/S Ferrosan, Soborg, Denmark

[21] Appl. No.: 118,399

[22] Filed: Nov. 9, 1987

[30] Foreign Application Priority Data

Nov. 11, 1986 [GB] United Kingdom ................. 8626936

[51] Int. Cl.⁴ .................... A61U 31/44; A61U 31/445
[52] U.S. Cl. ..................................... 514/326; 514/282
[58] Field of Search .......................................... 514/326

[56] References Cited

FOREIGN PATENT DOCUMENTS 0152273 8/1985 European Pat. Off. .

Primary Examiner—Stanley J. Friedman
Attorney, Agent, or Firm—Hopgood, Calimafde, Kalil, Blaustein & Judlowe

[57] ABSTRACT

A method for treating pain in human or non-human animals, which comprises administering an effective, non-toxic amount of paroxetine or a pharmaceutically acceptable salt thereof, to a sufferer.

7 Claims, No Drawings

TREATMENT OF PAIN WITH A PIPERIDINE

The present invention relates to a method for the treatment of pain and to a compound for use in such method.

U.S. Pat. No. 4,007,196 discloses the compound, (−)-trans-4-(4′-fluorophenyl)-3-(3′4′-methylenedioxyphenoxymethyl)piperidine, and, in Example 2, a process by which it can be prepared. The compound, which is referred to herein by its common name, paroxetine, is described in the patent as an inhibitor of 5-hydroxytryptamine uptake and, therefore, is of use in the treatment of depression. The patent also mentions that paroxetine is useful in the treatment of Parkinson's disease.

It has now been discovered that paroxetine also has potential therapeutic utility as an analgesic.

Accordingly, the present invention provides a method for treating pain in human or non-human animals, which method comprises administering an effective, non-toxic amount of paroxetine or a pharmaceutically acceptable salt thereof, to human or non-human animals suffering from pain.

The present invention also provides the use of paroxetine or a pharmaceutically acceptable salt thereof in the preparation of a medicament for use in the treatment of pain.

Examples of pharmaceutically acceptable salts of paroxetine are paroxetine hydrochloride, paroxetine hydrobromide, paroxetine acetate and paroxetine maleate. A preferred salt is crystalline paroxetine hydrochloride hemi-hydrate.

Because of its well-known anti-depressant effects, and new method for treating pain as disclosed herein, paroxetine has a particularly useful potential utility for the treatment of cancer patients, where depression and pain are common associated symptoms, and this represents a preferred use of paroxetine according to the invention.

Paroxetine additionally has a use in potentiating morphine analgesia, and thus has a role as an adjunct to morphine therapy in the relief of pain. It is to be understood that this aspect of pain control is also within the scope of the present invention.

A paroxetine medicament, for use in the treatment of pain may be prepared by admixture of paroxetine or salt thereof with an appropriate carrier, which may contain a diluent, binder, filler, disintegrant, flavouring agent, colouring agent, lubricant or preservative in conventional manner.

Preferably, the medicament is in unit dosage form and in a form adapted for use in the medical or veterinarial fields. For example, such preparations may be in a pack form accompanied by written or printed instructions for use as an agent in the treatment of pain.

The suitable dosage range for paroxetine or a salt depends on the nature of the pain and on the condition of the patient. It will also depend, inter alia, upon the relation of potency to absorbability and the frequency and route of administration.

Paroxetine or a salt thereof may be formulated for administration by any route, and examples are oral, rectal, topical, parenteral, intravenous or intramuscular administration. Preparations may, if desired, be designed to give slow release of paroxetine.

The medicaments may, for example, be in the form of tablets, capsules, sachets, vials, powders, granules, lozenges, reconstitutable powders, or liquid preparations, for example solutions or suspensions, or suppositories.

The medicaments, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycerine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid medicaments may be obtained by conventional methods of blending, filling, tabletting or the like. Repeated blending operations may be used to distribute paroxetine or a salt thereof throughout those medicaments employing large quantities of fillers. When the medicament is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The medicament may also be in the form of an ingestible capsule, for example of gelatin containing paroxetine or a salt thereof if desired with a carrier or other excipients.

Medicaments for oral administration as liquids may be in the form of, for example, emulsions, syrups, or elixirs, or may be presented as a dry product for reconstitution with water or other suitable vehicle before use. Such liquid medicaments may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

Paroxetine or a salt thereof may also be administered by a non-oral route. In accordance with routine pharmaceutical procedure, the medicaments may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or a solid form or concentrate which can be used to prepare an injectable formulation.

As mentioned hereinbefore, the effective dose of paroxetine depends on the nature of the pain, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of paroxetine and be administered in multiples, if desired, to give the preceding daily dose.

The present invention further provides a pharmaceutical composition for use in the treatment of pain which comprises an effective amount of paroxetine or a pharmaceutically acceptable salt thereof and a pharmaceutically acceptable carrier. Such compositions may be prepared in the manner as hereinbefore described.

The efficacy of paroxetine in treating pain is illustrated by the following animal tests, based on the method of Bianchi, C. and Franceschini, J. (Brit. J. Pharmacol. 9, 280, (1954).

Method

Groups of male T/O mice (Tuck (19–30 g) were selected for those that reacted within five seconds by attempting to bite an artery clip applied 1 cm from the base of the tail. The clip was re-applied at intervals after compound dosing and animals failing to respond within twenty seconds were considered to be exhibiting analgesia.

For the interaction studies paroxetine or vehicle was administered orally 30 minutes prior to morphine or vehicle subcutaneously and testing was initiated after another 30 minutes.

The results are shown in Tables 1 and 2.

TABLE 1

Antinociceptive Properties of Paroxetine Mouse Tail Clip Test

| Treatment (n = 10) | Dose mg/kg s.c. | % of animals not responding to tail clip, at times 30, 60 and 120 minutes | | |
|---|---|---|---|---|
| | | 30 | 60 | 120 |
| Paroxetine | 30 | 30 | 40 | 50 |
| | 10 | 20 | 20 | 50 |
| | 3 | 40 | 30 | 30 |
| Saline | — | 10 | 10 | 0 |

TABLE 2

Interaction of Paroxetine with Morphine-Induced Antinociception (Mouse Tail Clip Test)

| Treatment (n = 10) | | % of mice not responding to tail clip | |
|---|---|---|---|
| Drug | Dose mg/kg s.c. | Drug alone | Drug with paroxetine 5 mg/kg p.o. (30' prior) |
| Morphine | 12 | 70 | — |
| | 6 | 20 | 100 |
| | 3 | — | 50 |
| Saline | — | 0 | 10 |

Conclusions

Table 1 shows that paroxetine, administered from 3 to 30 mg/kg s.c., shows analgesic activity. Additonally, Table 2 shows that paroxetine administered at 5 mg/kg p.o. potentiates the analesic activity of morphine, administered at 6 mg/kg s.c.

I claim:

1. A method for treating pain in human or non-human animals, which comprises administering a pain relieving effective, non-toxic amount of paroxetine or a pharmaceutically acceptable salt thereof, to a human or non-human animal in need thereof.

2. A method according to claim 1, which comprises the administration of paroxetine or a pharmaceutically acceptable salt thereof by way of oral administration or parenteral administration.

3. A method according to claim 1, which comprises the administration of a unit dose containing from 20 to 1000 mg of paroxetine or a pharmaceutically acceptable salt thereof.

4. A method according to claim 1, wherein the pharmaceutically acceptable salt is selected from the group consisting of: paroxetine hydrochloride, paroxetine hydrobromide, paroxetine acetate and paroxetine maleate.

5. A method according to claim 4, wherein the salt is crystalline paroxetine hydrochloride hemihydrate.

6. A method according to claim 1, in which paroxetine or the salt is administered to a cancer sufferer.

7. A method according to claim 1, in which paroxetine or the salt is administered as an adjunct to morphine therapy.

* * * * *